(12) United States Patent
Kalies

(10) Patent No.: US 7,165,077 B2
(45) Date of Patent: Jan. 16, 2007

(54) METHOD FOR PROCESSING AND ORGANIZING PHARMACY DATA

(75) Inventor: Ralph F. Kalies, Picket, WI (US)

(73) Assignee: Omnicare, Inc., Covington, KY (US)

( * ) Notice: Subject to any disclaimer, the term of this patent is extended or adjusted under 35 U.S.C. 154(b) by 325 days.

(21) Appl. No.: 10/681,955

(22) Filed: Oct. 8, 2003
(Under 37 CFR 1.47)

(65) Prior Publication Data
US 2005/0071193 A1     Mar. 31, 2005

Related U.S. Application Data

(60) Provisional application No. 60/416,810, filed on Oct. 8, 2002.

(51) Int. Cl.
*G06F 17/30* (2006.01)
(52) U.S. Cl. .................................. 707/104.1
(58) Field of Classification Search ............. 707/1–10, 707/100–104.1, 200–206; 715/853; 705/26; 600/300
See application file for complete search history.

(56) References Cited

U.S. PATENT DOCUMENTS

| | | | |
|---|---|---|---|
| 4,799,156 A * | 1/1989 | Shavit et al. ................. 705/26 |
| 5,471,382 A * | 11/1995 | Tallman et al. .............. 600/300 |
| 5,613,106 A | 3/1997 | Thurman et al. |
| 5,706,494 A | 1/1998 | Cochrane et al. |
| 5,754,111 A | 5/1998 | Garcia |
| 5,832,450 A | 11/1998 | Myers et al. |
| 5,948,040 A | 9/1999 | DeLorme et al. |
| 6,339,832 B1 | 1/2002 | Bowman-Amuah |
| 6,343,323 B1 | 1/2002 | Kalpio et al. |
| 6,453,314 B1 | 9/2002 | Chan et al. |
| 6,625,590 B1 * | 9/2003 | Chen et al. .................... 707/1 |
| 6,724,408 B1 * | 4/2004 | Chen et al. ................. 715/853 |
| 6,732,331 B1 | 5/2004 | Alexander |
| 2002/0016717 A1 | 2/2002 | Ponzio, Jr. |
| 2002/0023086 A1 | 2/2002 | Ponzio, Jr. |
| 2002/0023169 A1 | 2/2002 | Ponzio, Jr. |
| 2002/0099273 A1 | 7/2002 | Bocionek et al. |
| 2002/0126812 A1 | 9/2002 | Majewski et al. |
| 2002/0128862 A1 | 9/2002 | Lau et al. |
| 2002/0129031 A1 | 9/2002 | Lau et al. |
| 2002/0129039 A1 | 9/2002 | Majewski et al. |
| 2002/0184133 A1 | 12/2002 | Zangari et al. |
| 2003/0014280 A1 | 1/2003 | Jilinskaia et al. |

\* cited by examiner

*Primary Examiner*—Diane D. Mizrahi
(74) *Attorney, Agent, or Firm*—Ostrolenk, Faber, Gerb & Soffen, LLP

(57) ABSTRACT

A method for processing and organizing pharmaceutical data from a plurality of sources. Batch files are submitted to a data processor electronically, such as via an electronic communications network. The batch files are checked for validity, then stored in a holding database. Records are read from the batch file and checked for errors such as relational integrity. Records having errors are noted in an exception file and held for correction, while records having no defects are placed into a common format and loaded into a data warehouse. Records having minor defects may also be loaded into the data warehouse pending correction of the defects.

22 Claims, 4 Drawing Sheets

METHOD FOR PROCESSING AND ORGANIZING PHARMACY DATA

This application claims priority to U.S. Provisional Application 60/416,810, filed Oct. 8, 2002, the contents of which are hereby incorporated by reference.

FIELD OF THE INVENTION

This invention relates to a method for managing pharmacy data. Specifically, the invention relates to a method for collecting pharmacy data from various sources, determining the integrity of the data, resolving problems with faulty data, and organizing the data to facilitate logical queries and analysis.

BACKGROUND OF THE INVENTION

The practice of pharmacy has undergone radical change in recent years, with a paradigm shift from small, independent pharmacies to regional and national networks of Publicly-held Corporate Pharmacies ("PCPs"). The advent of PCPs was in response to a desire by the industry to minimize the cost of drug therapy while maximizing profitability. Under the PCP system, much of the decision-making power is shifted from health care providers, such as physicians, to an administrative organization that establishes standards of care, standardizes methods of delivering care, and evaluates the outcomes of the care given. PCPs work to minimize costs and maximize profits through a variety of means, including volume purchases, quality control, "formulary" lists of preferred medications, rebates for movement of market share, and negotiated medical fees.

As part of the PCPs' focus on reducing the cost of health care and maximizing profitability, there is a high degree of interest in acquiring as much historical and timely ongoing data as possible regarding drug use and benefit, comparative costs of alternate therapies, and patient demographics. This information is preferably collected, organized, and stored in a "data warehouse." A data warehouse is a process by which large quantities of related data from many operational systems is merged into a single, standard repository to provide an integrated information view based on logical queries. Types of logical queries may relate to "data mining," which can be defined as a process of data selection, exploration and building models using vast data stores to discover previously unknown patterns. Other queries may be in support of research on a particular subject, such as relationships between particular diseases and patient demographics. An accurate and timely data warehouse is a valuable tool that can provide information for use in a wide variety of therapeutic, statistical, and economic analyses and interventions to aid the PCP medical and business staffs in making health care and business related decisions. The data warehouse can also provide feedback regarding the impact of prior decisions on outcomes and profitability, facilitating improvements in patient care, operational efficiency, and reducing the cost of medical care. In the prior art, stored data from the various operational and software systems must be converted to the software operating system used by the data warehouse in order to make the data usable for queries. This conversion process can be time-consuming and expensive, and may lead to disposing of a great deal of partial data records, especially given the large quantity of non-standardized data handled by data warehouses.

Most PCPs are comprised of formerly independent pharmacies and franchises, many having varying proprietary systems and formats for keeping pharmacy records. When those pharmacies are merged into a larger pharmacy network, it is desirable in many cases to maintain these systems rather than replace them, due to the large expense and operational burden associated with purchasing and implementing a new system. A particular problem thus faced by PCPs is how to check records generated by the proprietary systems for validity, standardize them, and organize them for use in a data warehouse. If the data accumulated by the data warehouse is defective, untimely or incomplete, decisions based on the data may likewise be incorrect, incomplete, or untimely. This can cause the PCP to incur increased costs and have profits that are not maximized. Thus, there is an ongoing need for a method for efficiently collecting pharmacy records from various sources, resolving problems with faulty or incomplete records, and organizing the records to facilitate querying and analysis.

SUMMARY OF THE INVENTION

According to the present invention, a method is disclosed for processing and organizing pharmacy data. Batch files containing a plurality of records are provided to a data processor by various sources, such as pharmacies. The data processor first checks the batch file for validity. The validity check may examine the file for defects in the "header," a section of the file containing information such as the source and the date range of the records in the file. Defective or missing information regarding such items as record type identification, dates, and submitter identification may be considered to be "fatal" errors. If fatal errors are found, processing stops and the data is not used. A message is sent to the submitting pharmacy by the data processor notifying them of the problem and requesting correction of the errors. In some cases, errors may be resolved through interpolation of the remaining data.

If the batch file passes the initial validity check, the records in the file are then loaded into a "holding database" for temporary storage. The records are then checked for errors, such as invalid formats for dates and monetary amounts. An exception table is created to tabulate the errors. If a record generates an error, the problem is noted in the exception table and the record is "quarantined" in the holding database pending resolution of the problem. Records free of errors are passed to the data warehouse.

BRIEF DESCRIPTION OF THE DRAWINGS

Further features of the present invention will become apparent to those skilled in the art to which the present invention relates from reading the following specification with reference to the accompanying drawings, in which.

DESCRIPTION OF THE PREFERRED EMBODIMENTS

In the discussion that follows it should be noted that structural components of the present invention are identified with numerals, while steps, tasks or actions are identified with numerals having a prefix "s." In addition, the same numerals are used in the various embodiments described below where the numerals refer to the same components and/or steps.

Figure 1:
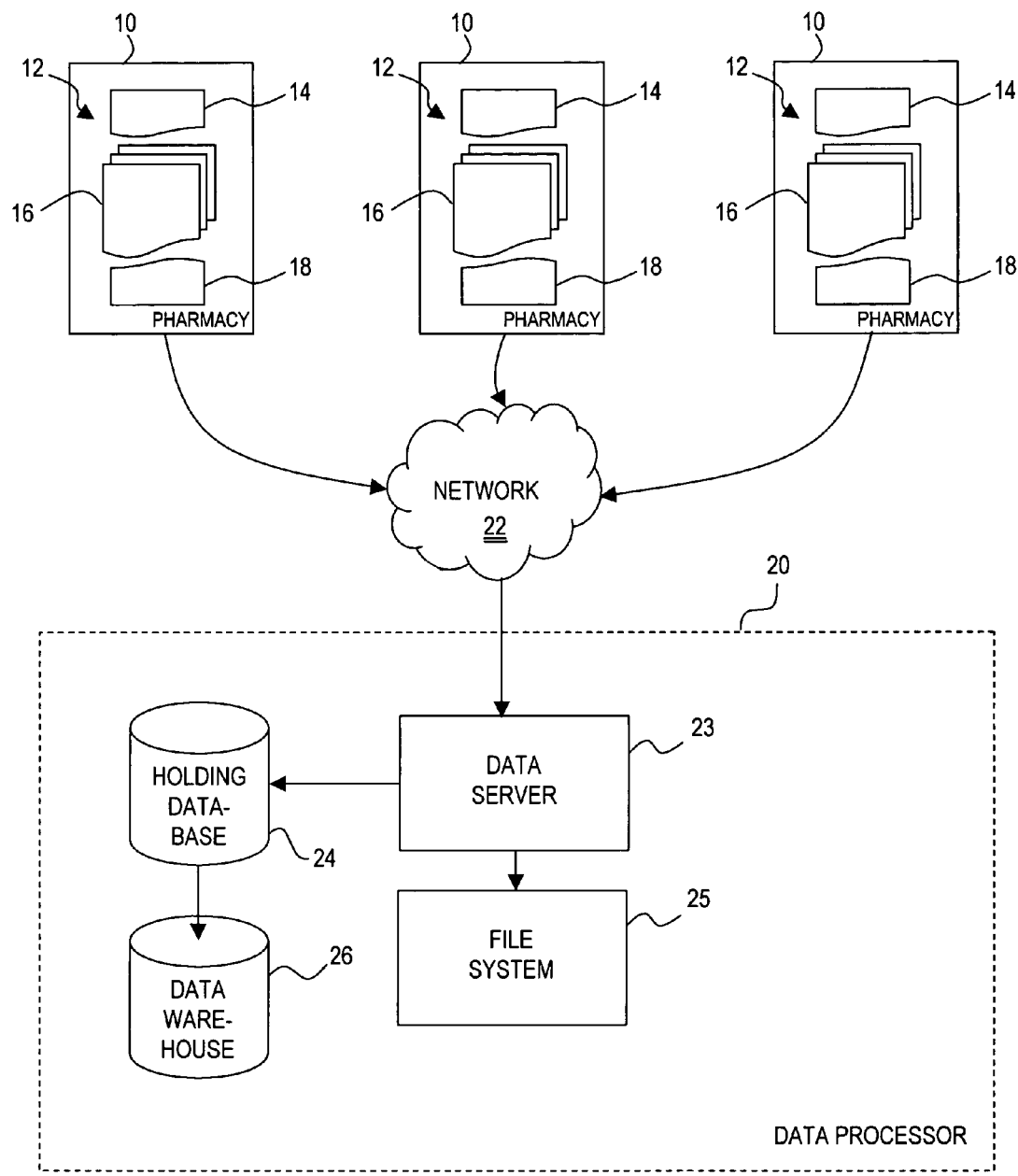
FIG. 1 is a flow diagram showing the collection of pharmacy data from various sources according to an embodiment of the present invention.

A flow diagram of a method for collecting pharmacy data from a plurality of various data sources is shown in FIG. 1. The data sources, as at 10 are typically retail pharmacies, health care facilities, medical facilities, health care personnel and patients within a pharmacy benefits network. The data sources 10 will each assemble batch files 12 comprising a header 14, at least one pharmacy record 16 and a trailer 18. Header 14 and trailer 18 may provide the recipient of the batch file 12 with information such as the number and type of pharmacy records 16, record date range, data integrity information, and processing instructions. Pharmacy records 16 may also include: details regarding the pharmacy facility and personnel; payment plan information; patient information such as demographics, diagnoses, diets, allergies, and lab codes; medical record codes; prescription and dispensing records; patient outcomes; and customer demographics and transactions. The assembled batch files are transmitted to a data processor 20 via an electronic communications network 22. Electronic communications network 22 may be any type of wired or wireless electronic computer network, including but not limited to, the Internet, Virtual Private Networks ("VPN"), extranets and intranets, local area networks ("LAN") and wide area networks ("WAN"). Data processor 20 receives pharmacy data via a data server 23 and processes batch files 12 using a file system 25, as will be discussed in detail below. A holding database 24 temporarily stores files, as at 12, during processing. Pharmacy records 16 that have been validated and found free of fatal errors are passed along and stored in a data warehouse 26.

Figure 2:
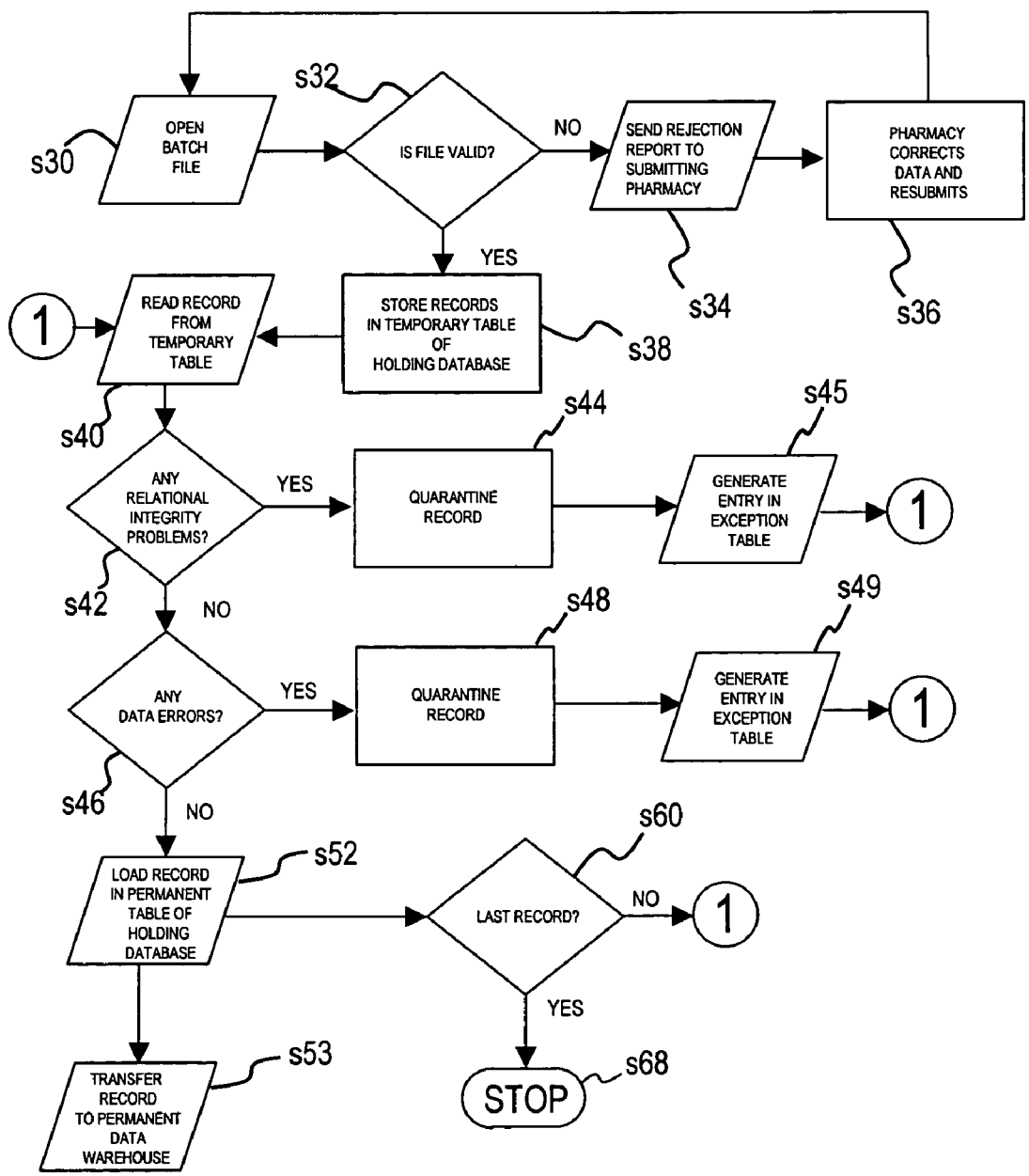
FIG. 2 is a flow diagram of a method for processing and organizing pharmacy data according to an embodiment of the present invention.

With reference to FIG. 2 and continued reference to FIG. 1, a flow diagram of a method for processing and organizing pharmacy data is depicted according to an embodiment of the present invention. At s30, a batch file 12 submitted by a pharmacy 10 is opened by data processor 20. Before processing of the pharmacy records 16 is attempted, an initial check of the validity of the file 12 is made at s32. Standards are defined for the validity check at s32, including faults such as file naming convention errors and defects or missing information in file header 14 and/or trailer 18. If unresolvable problems are encountered, processing of file 12 is halted and an error report is sent to the pharmacy that submitted the data, as indicated at s34. Since participation of the majority of data sources is within a network is key to its success, pharmacy 10 is then directed to correct and resubmit the file 12 to the data processor 20, as at s36. If no problems are detected, records 16 of file 12 are stored in a temporary table of holding database 24, as at s38, for further processing. At s40 a record 16 in holding database 24 is read. The record 16 is checked for relational data integrity, as at s42, by comparing the submitted data to defined standards within a file system 25. The file system 25 The defined standards of file system 25 may include criteria pertaining to record types, formatting standards for data fields, information for matching data to customers, row level constraints, and data length constraints. If a relational integrity problem is detected at s42, the record may be quarantined in the holding database 24, as shown at s44, pending resolution of the problem by the transmitting pharmacy and/or the data processor. In addition, an entry may be made in an exception table as shown at s45. An "exception table" may be defined herein as a listing of records having one or more problems or errors that require some sort of corrective action. If no relational integrity problems are found, the record 16 is checked for data errors, as at s46. Such errors may include invalid dates, codes, or amounts, missing data, wrong character/number type for given fields, and non-null fields. If data errors are found, the record 16 may be quarantined in the holding database 24 as at s48, pending resolution of the problem. In addition, an entry may be made in the exception table, as at s49. If no errors are detected, the accepted record 16 is loaded into a permanent table of holding database 24, as at step s52. The accepted record 16 is then transferred from the permanent table of holding database 24 to data warehouse 26, as at step s53. It should be noted that the transfer of the accepted record 16 at step s53 may occur asynchronously with steps s30–s52. The records added to data warehouse 26 are stored in a predetermined organizational format to facilitate later queries and analyses.

A check for the last record 16 in the file 12 is made, as at step s60. If the last record 16 has not been read, the next record is read, as at s40, repeating the aforesaid steps. If the last record 16 has been read, the exception table is checked for any entries, as at s62. If the exception table does contain entries, the submitting pharmacy 10 may be notified with a corrective action request, as at s66, to resolve any errors and/or warnings. The processing of file 12 is completed at s68.

In use, once the pharmacy records 16 have been processed and organized in data warehouse 26, the data contained therein may be used as an analytical tool for therapeutic and economic decision-making by appropriate personnel. In particular, data warehouse 26 provides a view of therapeutic and economic information over time, providing a perspective, including trending, not visible by examining discrete or small samples of a population of pharmacy records. Data warehouse 26 also provides means for monitoring the effects of prior decisions, facilitating "closed-loop" decision-making. For example, data regarding comparable courses of treatment protocols may be studied to optimize patient outcomes and eliminate expenses that do not positively contribute to the desired patient outcome.

The various steps in this embodiment of the present invention are preferably accomplished with the aid of at least one electronic computer (not shown).

Figure 3:
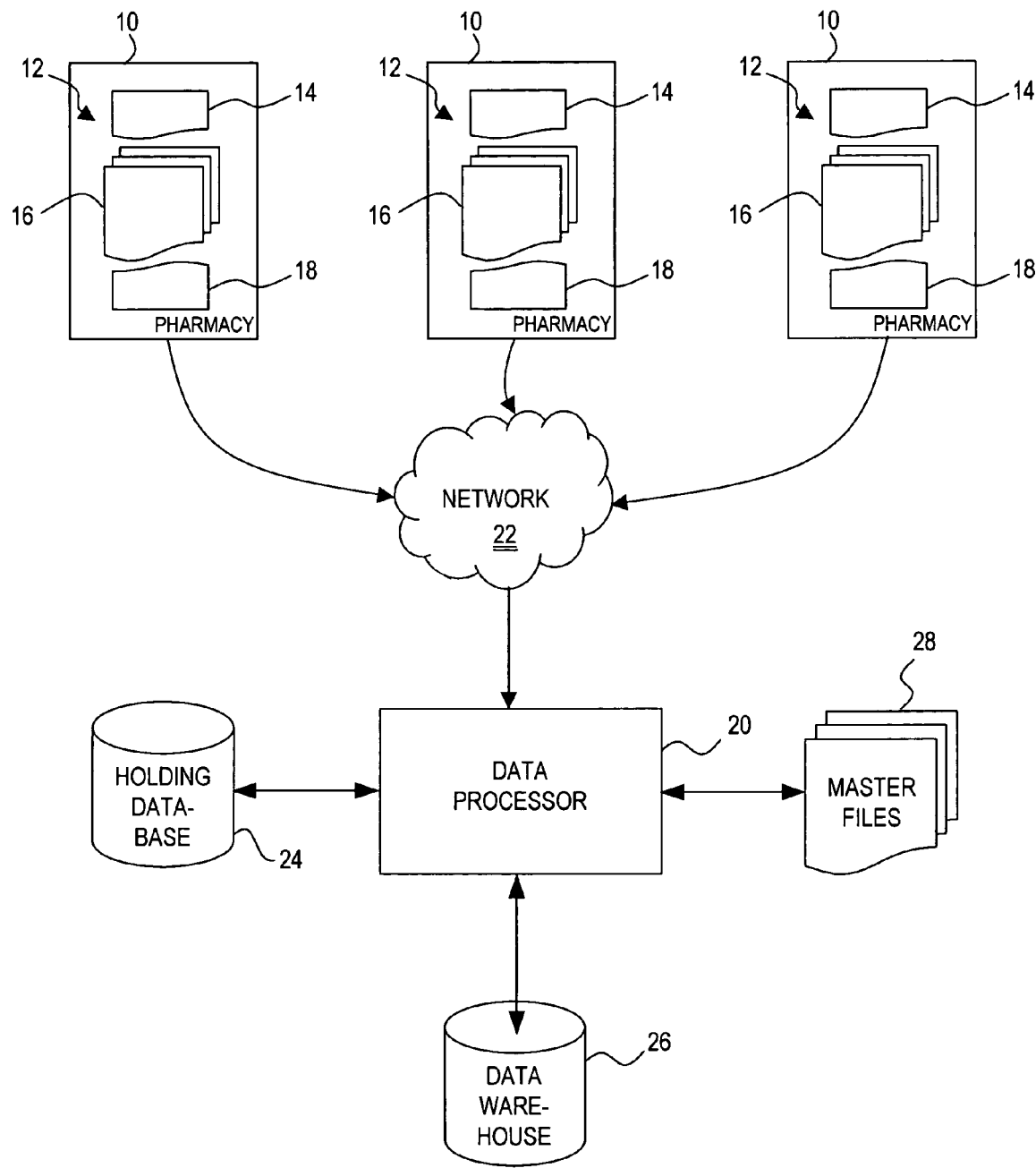
FIG. 3 is a flow diagram showing the collection of pharmacy data from various sources according to an alternate embodiment of the present invention.

A flow diagram of a method for collecting pharmacy data from a plurality of various sources according to an alternate embodiment of the present invention is shown in FIG. 3. The data sources, as at 10, are typically unrelated retail pharmacies, health care facilities, medical facilities, health care personnel and patients within a pharmacy benefits network, using available software programs. The data sources 10 will each assemble batch files 12 comprising a header 14, at least one pharmacy record 16 and a trailer 18. Header 14 and trailer 18 may provide the recipient of the batch file 12 with information such as the number and type of records 16, record date range, data integrity information, and processing instructions. Records 16 may include: details regarding the pharmacy facility and personnel; payment plan information; patient information such as demographics, diagnoses, diets, allergies, and lab codes; medical record codes; prescription and dispensing records; and customer demographics and transactions. The assembled batch files 12 are transmitted to a data processor 20 via an electronic communications network 22. Electronic communications network 22 may be any type of wired or wireless electronic computer network, including but not limited to, the Internet, Virtual Private Networks ("VPN"), extranets and intranets, local area networks ("LAN") and wide area networks ("WAN"). Data processor 20 receives and processes batch files 12 using a set of master files 28, as will be discussed in detail below. A holding database 24 temporarily stores file 12 during processing. Records 16 that are accepted after processing are transferred from holding database 24 and stored in a data warehouse 26.

Figure 4:
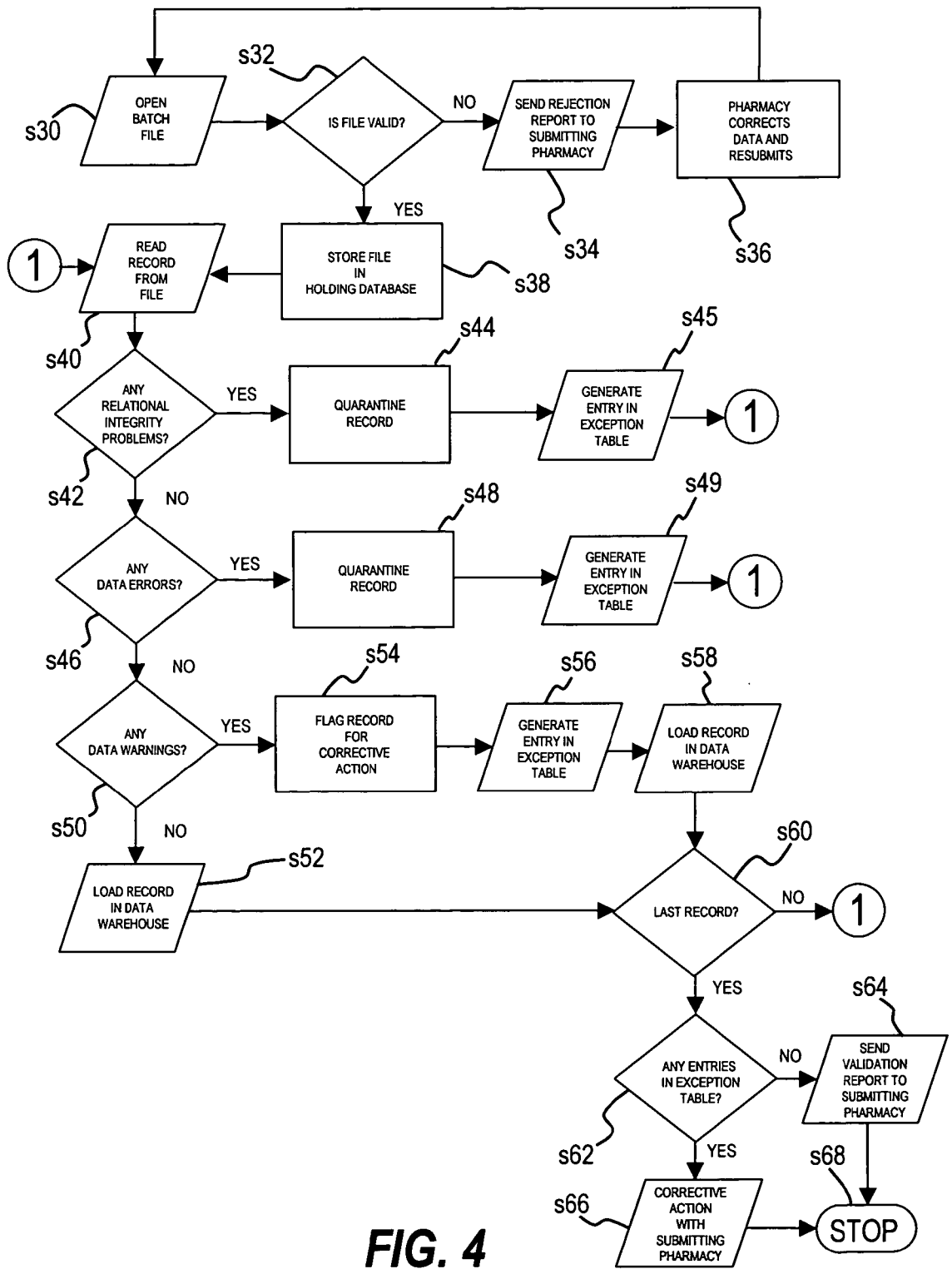
FIG. 4 is a flow diagram of a method for processing and organizing pharmacy data according to an alternate embodiment of the present invention.

With reference to FIG. 4 in combination with FIG. 3, a flow diagram of a method for processing and organizing pharmacy data is depicted according to an alternate embodiment of the present invention. At s30, an incoming batch file 12 submitted by a pharmacy 10 is examined by a data processor 20. Before processing of the records 16 is attempted, a check of the validity of file 12 is made at s32. Predetermined standards are stored for the validity check at s32, including faults such as file naming convention errors and defects or missing information in the file header 14 and/or trailer 18. If problems are detected, processing of file 12 is halted and an error report is sent to the submitting pharmacy 10, as indicated at s34. Pharmacy 10 then corrects and resubmits file 12 to the data processor 20, as at s36. If no problems are detected, file 12 is then stored in a temporary table of holding database 24, as at s38, for further processing. At s40 a first record 16 in file 12 is read. Record 16 is checked for relational data integrity, as at s42, by comparing the submitted data to pre-defined standards within at least one master file 28. The master files 28 are used as cross-references and may include such data as nursing facilities, patient demographics, payment plans, and patient allergies. The master files 28 may also contain criteria pertaining to formatting standards for data fields, information for matching data to customers, row level constraints, and data length constraints. If a relational integrity problem is detected at s42, the record may be quarantined in the holding database 24, as at s44, pending resolution of the problem by the transmitting pharmacy 10 and/or the data processor 20. In addition, an entry may be made in an exception table as shown at s45. If no relational integrity problems are found, the record 16 is checked for data errors, as at s46. Such errors may include invalid dates, codes, or amounts, missing data, wrong character/number type for given fields, and non-null fields. If data errors are found, the record 16 may be temporarily quarantined in the holding database 24 as at s48, pending resolution of the problem. In addition, an entry may be made in the exception table, as at s49. If no errors are detected, record 16 is then checked for any warnings, as at s50. Standards for warnings are predetermined, and may include non-existent lookup tables or invalid fields or codes such as DEA numbers, invalid "ICD9" standardized medical diagnosis codes, and invalid facilities. If no warnings are detected, record 16 is transferred to data warehouse 26, as at s52. If warnings are detected, record 16 is flagged for corrective action, as at s54, and an entry is made in the exception table, as at s56. However, a record 16 having warning flags is deemed to be acceptable for use pending corrective action and may be added to data warehouse 26, as at s58. Corrective actions for records 16 having warning flags may include changes to data extraction procedures by transmitting pharmacy 10 and/or data processor 20, resubmission of corrected data, and manual corrections by transmitting pharmacy 10 and/or data processor 20. Records 16 added to data warehouse 26 are stored in a predetermined organizational format to facilitate later queries.

Records 16 are then processed until the last record in the temporary table has been processed. A check for the last record 16 in file 12 is made, as at s60. If the last record 16 has not been read, the next record is read, as at s40, repeating the aforesaid steps. If the last record 16 has been read, the exception table is checked for any entries, as at s62. If no entries are found, a report is sent to the submitting pharmacy, as at s64, notifying submitting pharmacy 10 that batch file 12 was accepted and entered. If the exception table does contain entries, submitting pharmacy 10 is notified with a corrective action request, as at s66, to resolve the errors and/or warnings. The processing of batch file 12 is completed at s68.

In use, once the pharmacy records 16 have been processed and organized in the data warehouse 26, the data contained in the warehouse may be used as an analytical tool for therapeutic and economic decision-making, as previously discussed.

The various steps of this alternate embodiment of the present invention are preferably accomplished with the aid of at least one electronic computer not shown).

While this invention has been shown and described with respect to several detailed embodiments thereof, it will be understood by those skilled in the art that various changes in form and detail thereof may be made without departing from the scope of the claims of the invention. One skilled in the art will recognize that many of the separately-described functions of the various embodiments of the present invention may be combined, rearranged or eliminated to accomplish the desired result without affecting the scope of the invention. The embodiments disclosed herein are for illustrative purposes only and are not intended to be limiting with regard to the arrangement or combination of the components of the present invention.

What is claimed is:

1. A method for electronically processing and organizing pharmacy data for analysis, comprising the steps of:
   a) defining a first set of standards for determining the validity of a batch file containing at least one pharmacy record;
   b) defining a second set of standards for determining the relational integrity of each of the at least one pharmacy record in the batch file;
   c) defining a third set of standards for determining the presence of any data errors in each of the at least one pharmacy record;
   d) assembling at least one electronic batch file by a data source, the at least one electronic batch file comprising a header, at least one pharmacy record and a trailer;
   e) communicating the at least one electronic batch file from the data source to a data processor;
   f) checking by the data processor each of the at least one electronic batch file for validity in accordance with the first set of standards and either:
      i) rejecting a respective electronic batch file if it does not meet the first set of standards, and communicating a rejection report to the data source, or
      ii) accepting the respective electronic batch file if it meets the first set of standards, and storing at least one record from the electronic batch file in a temporary table of a holding database;
   g) reading a selected record from the temporary table;
   h) checking the selected record for relational integrity in accordance with the second set of standards, and if any relational integrity errors are found:

i) quarantining the selected record, and
ii) generating an entry in an exception table for the selected record;
i) checking the selected record for data errors in accordance with the third set of defined standards, and if any data errors are found:
i) quarantining the selected record, and
ii) generating an entry in the exception table for the selected record;
j) transferring the selected record to a permanent table of the holding database if no relational integrity or data errors are found;
k) repeating steps (g) through (j) until all records in the temporary table have been read; and
l) electronically transferring the records from the permanent table of the holding database to a data warehouse for selective access and analysis.

2. The method of claim 1 wherein communications between the data source and the data processor is via an electronic communications network.

3. The method of claim 1 wherein the at least one pharmacy record comprises patient and transaction data.

4. The method of claim 3 wherein the at least one pharmacy record comprises details regarding pharmacy facility and personnel, patient payment plan information, patient information, lab codes, medical record codes, and prescription, dispensing and transaction information.

5. The method of claim 1 wherein the validity check comprises checking the header for file-naming convention errors, defects and missing information.

6. The method of claim 1 wherein the checking of the selected record for data errors comprises examining for invalid dates, codes, or amounts, missing data, and wrong alpha-numeric characters in data fields.

7. The method of claim 1, wherein the data source further:
a) corrects the rejected batch file, and
b) communicates a corrected batch file to the data processor.

8. The method of claim 1 wherein the steps are accomplished with the aid of at least one computer.

9. A method for electronically processing and organizing pharmacy data for analysis, comprising the steps of:
a) defining a first set of standards for determining the validity of a batch file containing at least one pharmacy record;
b) defining a second set of standards for determining the relational integrity of each of the at least one pharmacy record in the batch file;
c) defining a third set of standards for determining the presence of any data errors in each of the at least one pharmacy record;
d) defining conditions for warnings regarding defects in each of the at least one pharmacy record;
e) assembling at least one electronic batch file by a data source, the at least one electronic batch file comprising a header, at least one pharmacy record and a trailer;
f) communicating the at least one electronic batch file from the data source to a data processor;
g) checking by the data processor each of the at least one electronic batch file for validity in accordance with the first set of standards and either:
i) rejecting a respective electronic batch file as a rejected batch file if it does not meet the first set of standards, and communicating a rejection report to the data source, or
ii) accepting a respective electronic batch file as a valid batch file if it meets the first set of standards, and storing the valid batch file in a holding database;
h) reading a selected record of the valid batch file;
i) checking the selected record for relational integrity in accordance with the second set of standards, and if any relational integrity errors are found:
i) quarantining the selected record, and
ii) generating an entry in an exception table for the selected record;
j) checking the selected record for data errors in accordance with the third set of defined standards, and if any data errors are found:
i) quarantining the selected record, and
ii) generating an entry in the exception table for the selected record;
k) checking the selected record for warnings, and if any warnings are found:
i) flagging the record for later corrective action, and
ii) generating an entry in the exception table for the selected record;
l) transferring each non-quarantined record to a permanent table of the holding database;
m) repeating steps (h) through (l) until all records in the valid batch file have been read;
n) communicating the non-quarantined records from the permanent table to a data warehouse for storage in a predetermined organizational format; and
o) undertaking corrective action for the entries in the exception table.

10. The method of claim 9 wherein communications between the data source and the data processor is via an electronic communications network.

11. The method of claim 9 wherein each of the at least one pharmacy record comprises patient and transaction data.

12. The method of claim 11 wherein each of the at least one pharmacy record comprises details regarding pharmacy facility and personnel, patient payment plan information, patient information, lab codes, medical record codes, and prescription, dispensing and transaction information.

13. The method of claim 9 wherein the validity check comprises checking the header for file-naming convention errors, defects and missing information.

14. The method of claim 9 wherein the checking of the selected record for data errors comprises examining for invalid dates, codes, or amounts, missing data, and wrong alpha-numeric characters in data fields.

15. The method of claim 9 wherein the warnings include ICD9 diagnosis codes, and invalid facilities.

16. The method of claim 9, wherein the data source further:
a) corrects the rejected batch file, and
b) communicates a corrected batch file to the data processor.

17. The method of claim 16 wherein the corrected batch file is communicated to the data processor via an electronic communications network.

18. The method of claim 9 wherein each of the at least one pharmacy record is checked for relational integrity by comparing the at least one pharmacy record to a master file.

19. The method of claim 9, further comprising the step of communicating a validation report to the data source.

20. The method of claim 19 wherein the report is communicated via an electronic communications network.

21. The method of claim 9, further comprising the step of querying the data warehouse.

22. The method of claim 9 wherein the steps are accomplished with the aid of at least one computer.

* * * * *